United States Patent
Hingston et al.

(10) Patent No.: US 9,993,582 B2
(45) Date of Patent: Jun. 12, 2018

(54) ADHESIVE STENT COATING FOR ANTI-MIGRATION

(71) Applicant: Boston Scientific Scimed, Inc., Maple Grove, MN (US)

(72) Inventors: John Hingston, Framingham, MA (US); Gary Jordan, Litchfield, NH (US); William Bertolino, Framingham, MA (US); Paul K. Norton, Lunenburg, MA (US); Jason Weiner, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 28 days.

(21) Appl. No.: 14/012,404

(22) Filed: Aug. 28, 2013

(65) Prior Publication Data

US 2014/0074219 A1    Mar. 13, 2014

Related U.S. Application Data

(60) Provisional application No. 61/700,008, filed on Sep. 12, 2012.

(51) Int. Cl.
| | | |
|---|---|---|
| *A61L 27/58* | (2006.01) | |
| *A61L 31/10* | (2006.01) | |
| *A61L 31/14* | (2006.01) | |

(52) U.S. Cl.
CPC ............ *A61L 27/58* (2013.01); *A61L 31/10* (2013.01); *A61L 31/148* (2013.01); *A61L 2420/02* (2013.01); *A61L 2420/08* (2013.01); *A61L 2430/36* (2013.01)

(58) Field of Classification Search
CPC ................. A61F 2/06; A61F 2002/072; A61F 2002/044; A61L 31/08; A61L 27/00; A61L 27/20; A61L 27/28; A61L 27/58; A61L 31/148; A61L 31/10; A61L 2420/08; A61L 2420/02; A61L 2430/36
USPC ....... 623/1.44, 1.45, 1.46, 1.53, 23.69, 23.7, 623/23.75, 23.76
See application file for complete search history.

(56) References Cited

U.S. PATENT DOCUMENTS

| | | | |
|---|---|---|---|
| 5,405,366 | A | 4/1995 | Fox et al. |
| 5,618,551 | A | 4/1997 | Tardy et al. |
| 5,693,034 | A | 12/1997 | Buscemi et al. |

(Continued)

FOREIGN PATENT DOCUMENTS

| | | |
|---|---|---|
| WO | 2000/040278 | 7/2000 |
| WO | 2006/038866 | 4/2006 |

OTHER PUBLICATIONS

U.S. Appl. No. 61/394,104, filed Oct. 18, 2010, inventor Rajesh Radhakrishnan et al.

(Continued)

*Primary Examiner* — Christopher D Prone
*Assistant Examiner* — Rokhaya Diop
(74) *Attorney, Agent, or Firm* — Seager, Tufte & Wickhem, LLP

(57) ABSTRACT

A stent, the stent including a first coating composition disposed on at least a portion of the outer surface of the stent, the first coating composition having at least one bioadhesive and a second coating composition disposed over the first coating composition, the second coating composition having at least one biodegradable polymer, and methods of making and using the same.

20 Claims, 9 Drawing Sheets

(56) References Cited

U.S. PATENT DOCUMENTS

| | | | |
|---|---|---|---|
| 5,749,880 A * | 5/1998 | Banas | A61F 2/07 606/198 |
| 6,176,849 B1 | 1/2001 | Yang et al. | |
| 6,251,136 B1 | 6/2001 | Guruwaiya et al. | |
| 6,379,379 B1 * | 4/2002 | Wang | A61F 2/82 623/1.15 |
| 6,447,835 B1 * | 9/2002 | Wang et al. | 427/2.24 |
| 6,589,215 B2 | 7/2003 | Yang et al. | |
| 6,610,035 B2 | 8/2003 | Yang et al. | |
| 6,624,245 B2 | 9/2003 | Wallace et al. | |
| 6,805,898 B1 | 10/2004 | Wu et al. | |
| 7,767,220 B2 | 8/2010 | Ranade et al. | |
| 8,114,147 B2 | 2/2012 | Wood et al. | |
| 8,147,866 B2 | 4/2012 | Finn et al. | |
| 8,221,783 B2 | 7/2012 | Helmus et al. | |
| 8,247,598 B2 | 8/2012 | Fang et al. | |
| 8,263,704 B2 | 9/2012 | Stopek et al. | |
| 2002/0065546 A1 * | 5/2002 | Machan et al. | 623/1.13 |
| 2003/0032734 A1 | 2/2003 | Roby | |
| 2004/0215169 A1 | 10/2004 | Li | |
| 2006/0069425 A1 | 3/2006 | Hillis et al. | |
| 2006/0167540 A1 * | 7/2006 | Masters et al. | 623/1.44 |
| 2006/0276887 A1 | 12/2006 | Brady et al. | |
| 2008/0009934 A1 | 1/2008 | Schneider et al. | |
| 2008/0071350 A1 | 3/2008 | Stinson | |
| 2008/0071358 A1 | 3/2008 | Weber et al. | |
| 2008/0286326 A1 * | 11/2008 | Benco | A61L 27/34 424/423 |
| 2009/0018648 A1 * | 1/2009 | Wittchow | 623/1.46 |
| 2009/0062927 A1 | 3/2009 | Marten et al. | |
| 2009/0082840 A1 | 3/2009 | Rusk et al. | |
| 2009/0098176 A1 | 4/2009 | Helmus et al. | |
| 2009/0187240 A1 * | 7/2009 | Clerc et al. | 623/1.17 |
| 2010/0069838 A1 | 3/2010 | Weber et al. | |
| 2010/0087783 A1 | 4/2010 | Weber et al. | |
| 2010/0121461 A1 * | 5/2010 | Sobrino-Serrano | A61F 2/04 623/23.68 |
| 2010/0316712 A1 | 12/2010 | Nangia et al. | |
| 2011/0160836 A1 * | 6/2011 | Behan | A61F 2/04 623/1.11 |
| 2011/0262520 A1 | 10/2011 | Dormady et al. | |
| 2011/0282437 A1 * | 11/2011 | Warner | A61F 2/915 623/1.44 |
| 2012/0035715 A1 | 2/2012 | Robida et al. | |
| 2012/0095396 A1 | 4/2012 | Radhakrishnan et al. | |
| 2012/0123521 A1 | 5/2012 | Headley, Jr. et al. | |
| 2012/0128793 A1 | 5/2012 | Miller et al. | |

OTHER PUBLICATIONS

Tao et al., "Bioadhesive poly(methyl methacrylate) microdevices for controlled drug delivery", Journal of Controlled Release, 88, (2003), 215-228.

http://en.wikipedia.org/wiki/Bioadhesive#Mucoadhesion.

Johanson et al., "Incidence and risk factors for biliary and pancreatic stent migration," Gastrointestinal Endoscopy, May-Jun. 1992; 38(3):341-6.

Lim et al., "The adhesive properties of coacervated recombinant hybrid mussel adhesive proteins", Biomaterials, 31, (2010), 3715-3722.

Park et al., "Mechanisms of Mucoadhesion of Poly(acrylic Acid) Hydrogels," Pharmaceutical research, 1987, vol. 4, No. 6, 457-464.

Dowding et al., "Preparation and Swelling Properties of Poly(NIPAM) "Minigel" Particles Prepared by Inverse Suspension Polymerization", Journal of Colloid and Interface Science 221, 268-272 (2000), available online at http:/www.idealibrary.com.

Sekiyama et al., "Novel Sutureless Transplantation of Bioadhesive-Coated, Freeze-Dried Amniotic Membrane for Ocular Surface Reconstruction", Investigative Ophthalmology & Visual Science, Apr. 2007, vol. 48, No. 4, 1528-1534.

Khutoryanskiy, "Advances in Mucoadhsion and Mucoadhesive Plymers," Macromolecular Bioscience, 2011, 11, pp. 748-764; Jim 14; 1J(6):748-64. doi: 10.1002/mabi.201000388.Epub Dec. 27, 2010.

\* cited by examiner

US 9,993,582 B2

ADHESIVE STENT COATING FOR ANTI-MIGRATION

CROSS-REFERENCE TO RELATED APPLICATIONS

This application claims priority to U.S. Patent Provisional Application No. 61/700,008, filed Sep. 12, 2012, the entire contents of which are hereby incorporated herein by reference.

BACKGROUND OF THE INVENTION

The present invention relates generally to a coated medical device and more particularly to a coated stent. Stents, grafts, stent-grafts, vena cava filters and similar implantable medical devices, collectively referred to hereinafter as stents, are radially expandable endoprostheses which are typically implants capable of being implanted transluminally and enlarged radially after being introduced percutaneously. Stents may be implanted in a variety of body lumens or vessels such as within the vascular system, esophagus, gastrointestinal tract, large and small intestine, biliary ducts, pancreas ducts, pulmonary and urinary tracts, etc. Stents may be used to reinforce body vessels and to prevent restenosis following angioplasty in the vascular system. Stents may also be used to open strictures. They may be self-expanding, mechanically expandable or hybrid expandable.

Stents are typically tubular members that are radially expandable from a reduced diameter configuration for delivery through a patient's body lumen to an expanded configuration once deployed at the treatment site.

Stents may be constructed from a variety of materials such as stainless steel, ELGILOY® (cobalt-chromium-nickel alloy), nickel, titanium, nitinol, shape memory polymers, other polymeric materials, etc. For metallic stents, a stent may be typically formed from a tubular member, either extruded or formed from a sheet, in which a pattern is subsequently formed by etching or cutting material from the tubular member.

Polymeric stents formed from a variety of thermoplastic polymer materials may be formed by weaving or braiding fibers or filaments.

Stents may further be provided with a cover, such as a silicone cover to prevent tissue ingrowth.

Desirable stent properties include sufficient flexibility to be able to conform to the tortuous body lumen during delivery, yet sufficiently rigid to resist migration once deployed at the treatment site.

In some stents, the compressible and flexible properties that assist in stent delivery may also result in a stent that has a tendency to migrate from its originally deployed position. Stent covering may contribute to migration as well. Stent migration affects many endoscopic stents including esophageal, pancreatic and biliary stents. Risk factors associated with stent migration are discussed in *Incidence and risk factors for biliary and pancreatic stent migration*, Johanson J F, Schmah. M J, Geenen J E. *Gastrointest Endosc.* 1992 May-June; 38(3):341-6.

It is thus desirable to provide a stent configuration that resists migration following deployment.

Commonly assigned US Patent Publication No. 20090098176, the entire content of which is incorporated by reference herein, discloses medical devices with triggerable bioadhesives.

SUMMARY OF THE INVENTION

In one aspect, the present invention relates to a stent including a first coating composition comprising at least one bioadhesive and a second coating composition disposed over the first coating composition, the second coating composition comprising at least one biodegradable polymer.

In another aspect, the present invention relates to a method of making a stent including the steps of providing a stent having an inner surface and an outer surface, applying a bioadhesive at least to a portion of said outer surface of said stent and applying a biodegradable coating over said bioadhesive.

These and other aspects, embodiments and advantages of the present disclosure will become immediately apparent to those of ordinary skill in the art upon review of the Detailed Description and Claims to follow.

DETAILED DESCRIPTION OF THE INVENTION

While embodiments of the present invention may take many forms, there are described in detail herein, specific embodiments of the present disclosure. This description is an exemplification of the principles of the present disclosure and is not intended to limit the disclosure to the particular embodiments illustrated herein.

Figure 1:
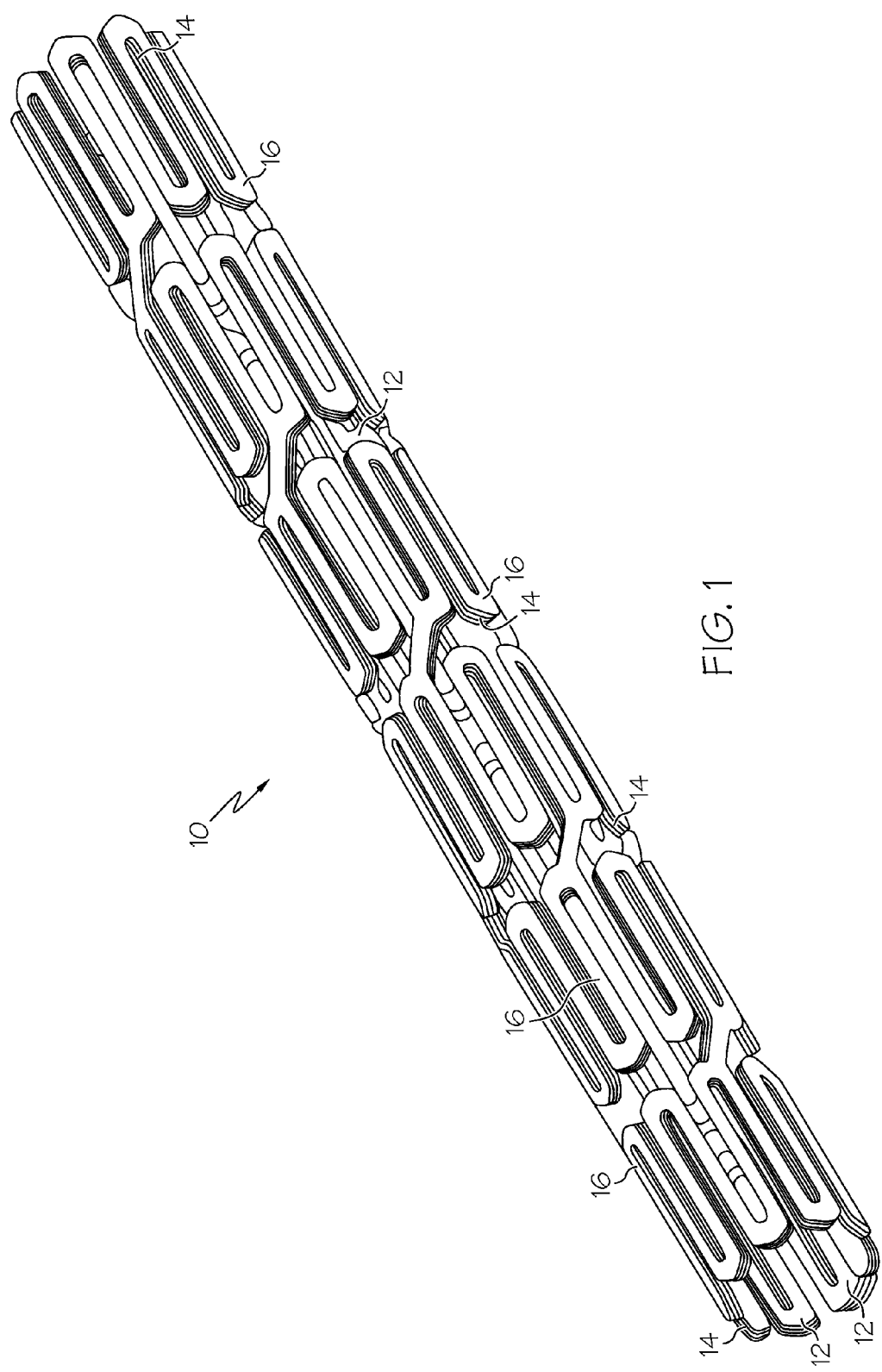
FIG. 1 is a perspective view of a stent 10 according to the invention in an unexpanded state.

Turning now to the drawings, FIG. 1 is a perspective view of a stent 10 according to the invention in an unexpanded state. Stent 10 is shown having a stent wall 12, a bioadhesive layer 14 and an outer biodegradable layer 16.

Figure 2:
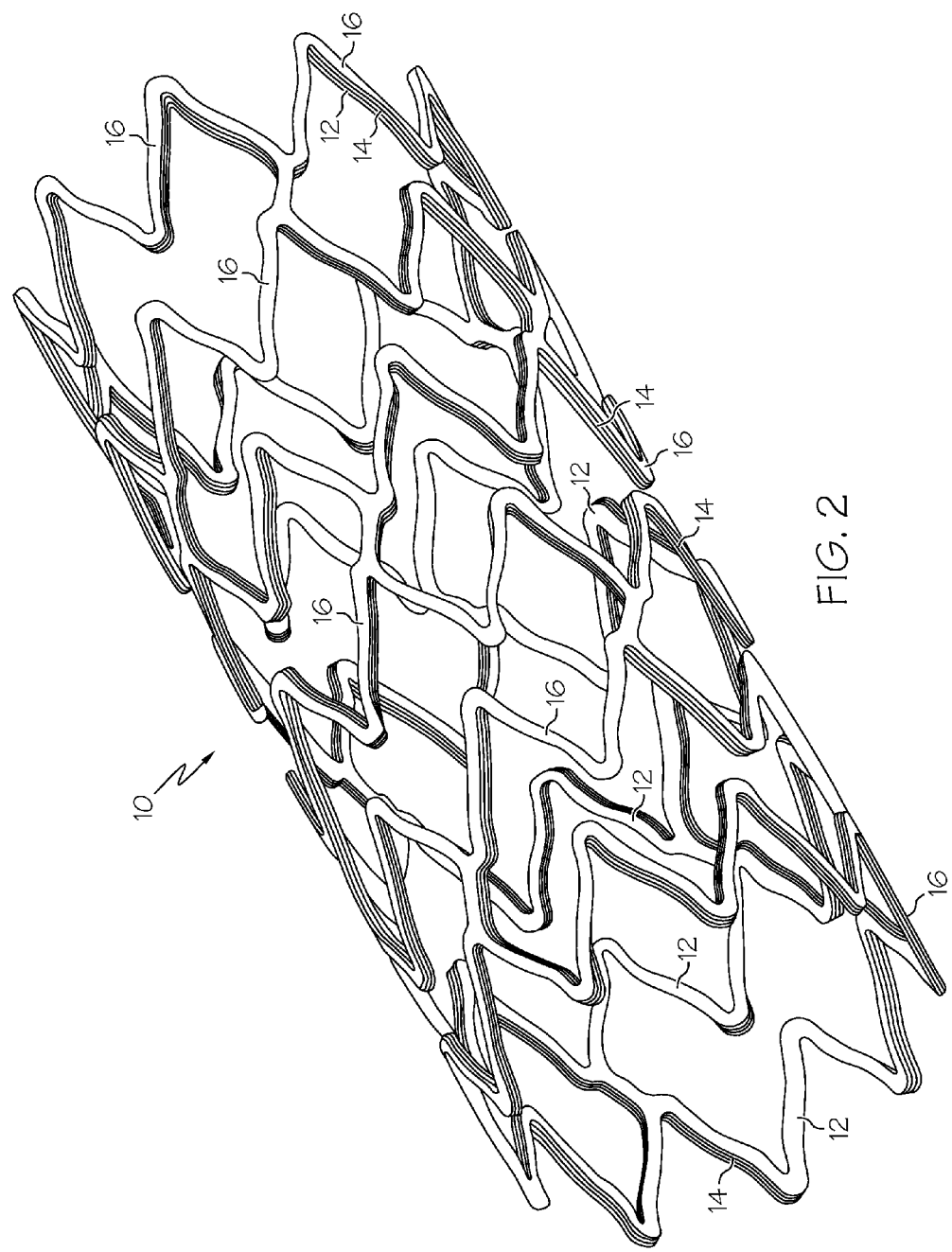
FIG. 2 is a perspective view of a stent 10 according to the invention in an expanded state.

FIG. 2 is a perspective view of a stent 10 according to the invention in an expanded state having a stent wall 12, a bioadhesive layer 14 and an outer biodegradable layer 16.

Figure 3:
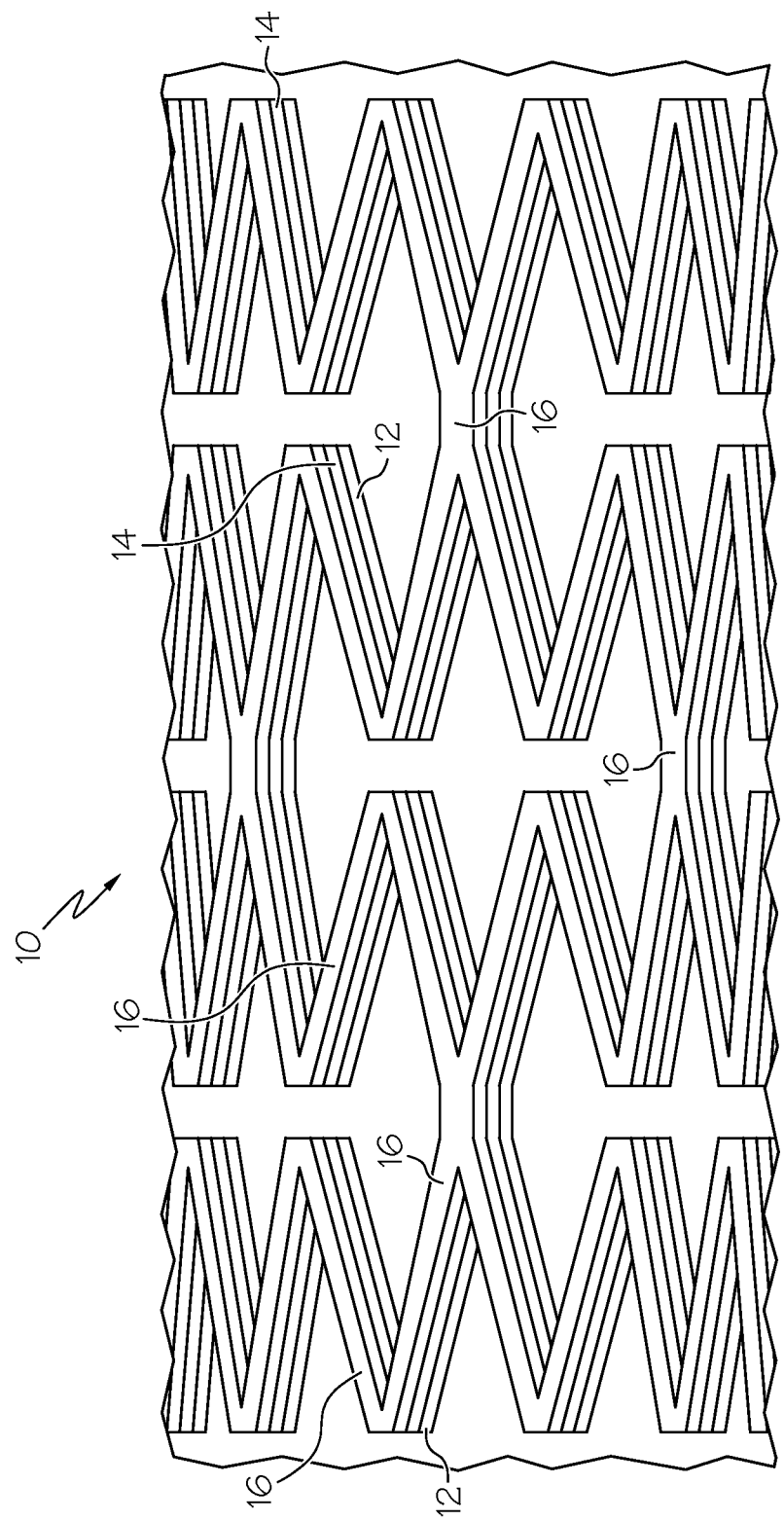
FIG. 3 is a partial enlarged view of a stent according to the invention.

FIG. 3 is partial enlarged view of a stent 10 having a stent wall 12, a bioadhesive layer 14 and an outer biodegradable layer 16.

Figure 4:
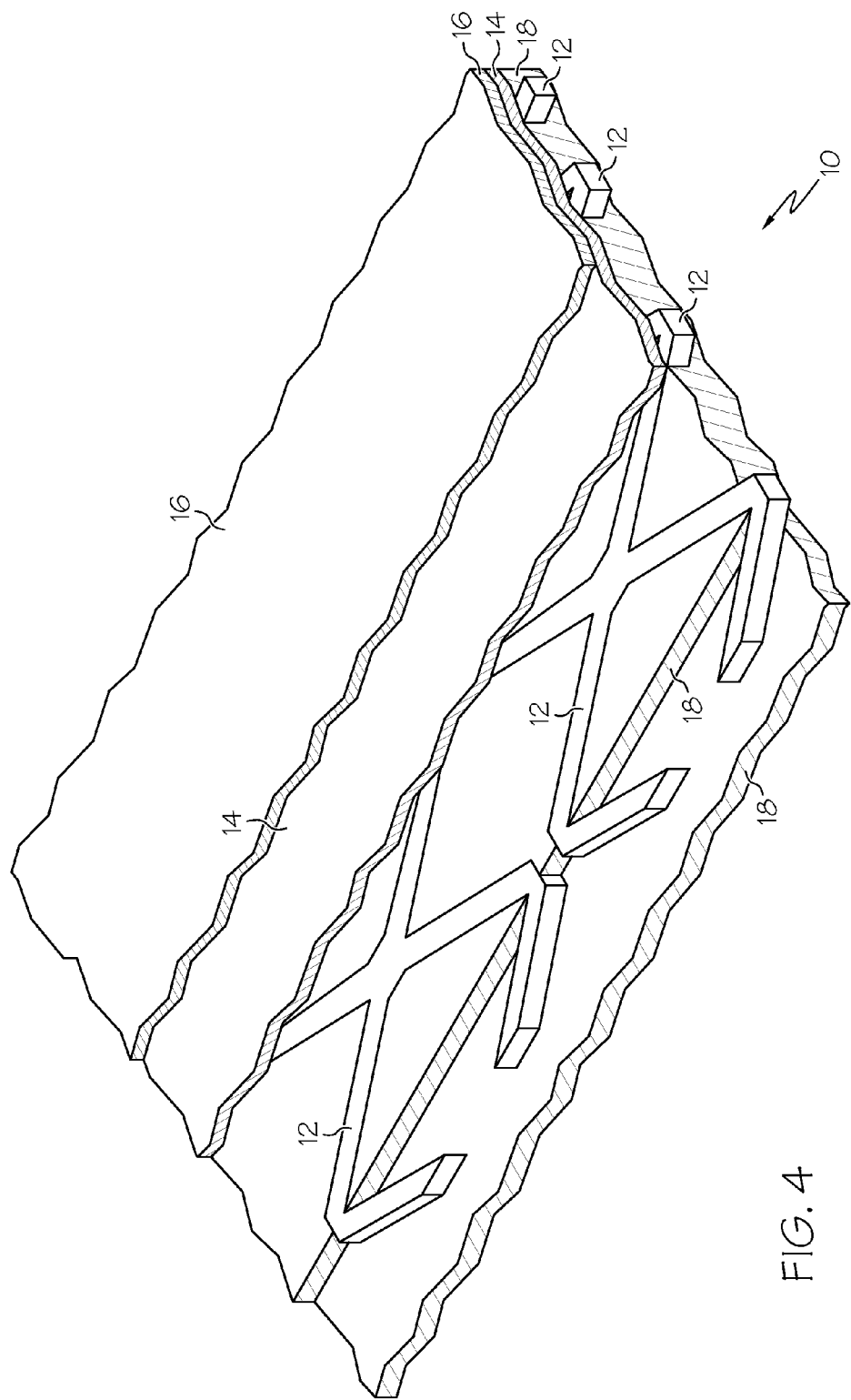
FIG. 4 is a partial enlarged view of an alternative embodiment of a stent according to the invention.

FIG. 4 is a partial enlarged view of a stent 10 having a stent wall 12 and disposed on the stent wall 12 is a bioadhesive layer 14 and an outer biodegradable layer 16. In this embodiment, stent 10 is shown also having a silicone covering 18 disposed on the inner surface of the stent wall 12 beneath.

Figure 5:
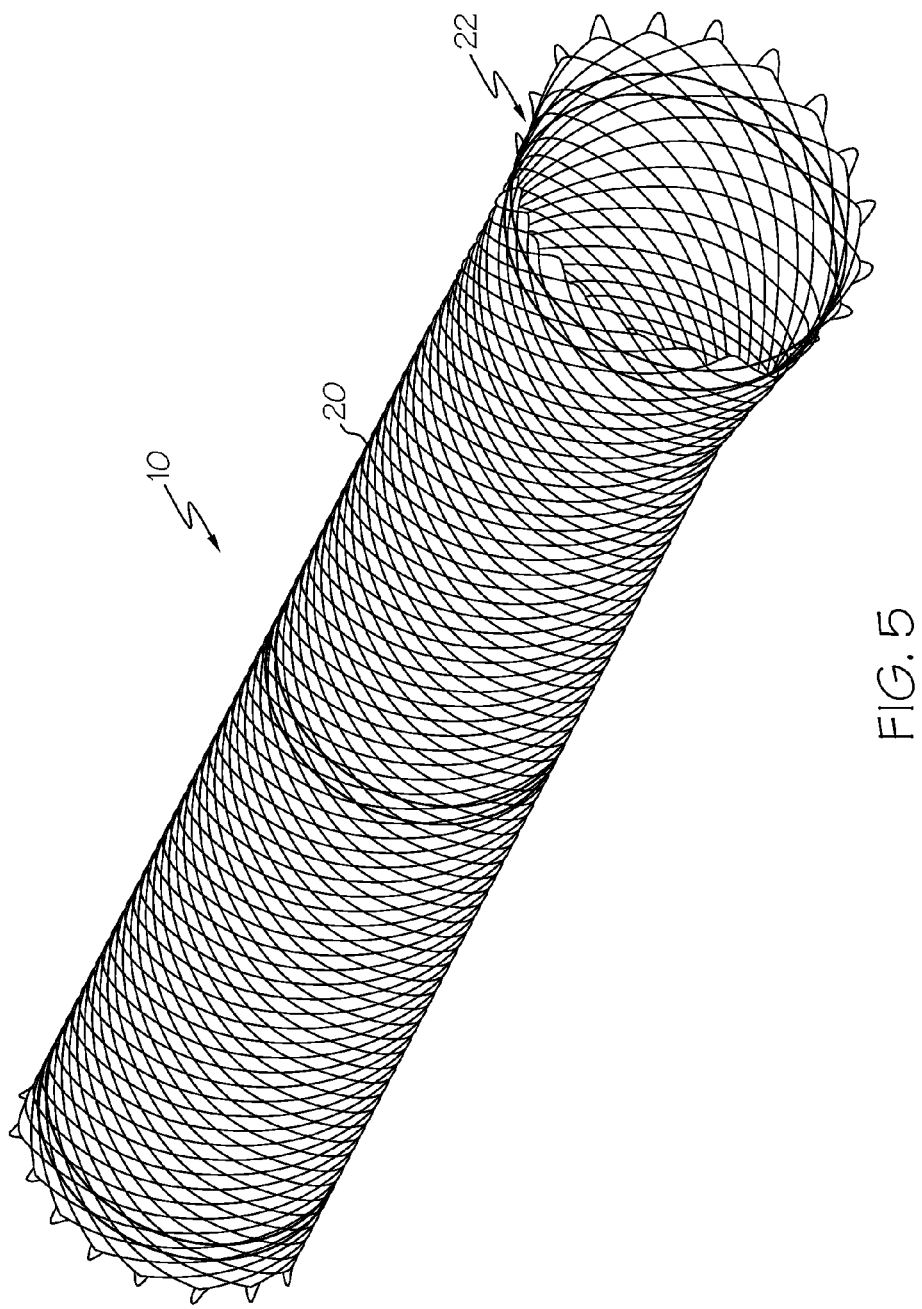
FIG. 5 is a perspective view of an exemplary stent on which the coatings may be employed.

FIG. 5 is a perspective view of an endoscopic stent 10 on which the coatings may be employed. Stent 10 may be coiled or patterned as a braided or woven open network or fibers or filaments as disclosed, for example, in commonly assigned US Patent Publication No. 2012/0128793, the entire content of which is incorporated by reference herein.

In one embodiment, stent 10 has a braided construction 20 and a flared proximal end 22. In this embodiment, stent 10 is an esophageal stent. Stent 10 may be formed of any suitable stent material including metallic and non-metallic materials as well as shape memory materials. Examples of suitable materials include, but are not limited to, shape memory alloys such as NITINOL® (nickel-titanium alloy), other metallic materials such as stainless steel, tantalum, titanium, nickel-chrome, or cobalt-chromium alloys such as those sold under the tradename of ELGILOY® (cobalt-chromium-nickel alloy).

Thermoplastic polymer materials which may be employed in forming the device include both elastomeric and non-elastomeric materials, examples of which include, but are not limited to, polyolefins such as metallocene catalyzed polyethylenes, polypropylenes, and polybutylenes and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; polycarbonates; and mixtures and block or random copolymers of any of the foregoing.

Stent 10 may also optionally be formed at least partially, or entirely of a biodegradable or bioabsorbable polymer material. Examples include, but are not limited to, poly (alpha-hydroxy acid) polymers and copolymers, such as polymers and copolymers of glycolide including polyglycolide (PGA), poly(glycolide-co-lactide)(PGLA), and poly (glycolide-co-trimethylene carbonate (PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly (lactide-co-trimethylene carbonate), poly(lactide-co-delta-valerolactone), poly(lactide-co-epsilon-caprolactone), poly (glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly (beta-dioxanone)(PDS); poly(delta-valerolactone); poly(epsilon-caprolactone); methylmethacrylate-N-vinylpyrrolidone copolymers; polyester amides; polyesters of oxalic acid; polydihydropyranes; poly(alkyl-2-cyano-acrylate); polyvinyl alcohol (PVA); polypeptides; poly(beta-maleic acid) (PMLA); poly(beta-alkanoic acid); poly(ethylene oxide) (PEO); polyanhydrides, polyphosphoester, and chitin polymers. See, for example, commonly assigned US Patent Publication No. 20120123521, the entire content of which is incorporated by reference herein. This patent also illustrates various stent designs which can be employed herein.

Figure 6:
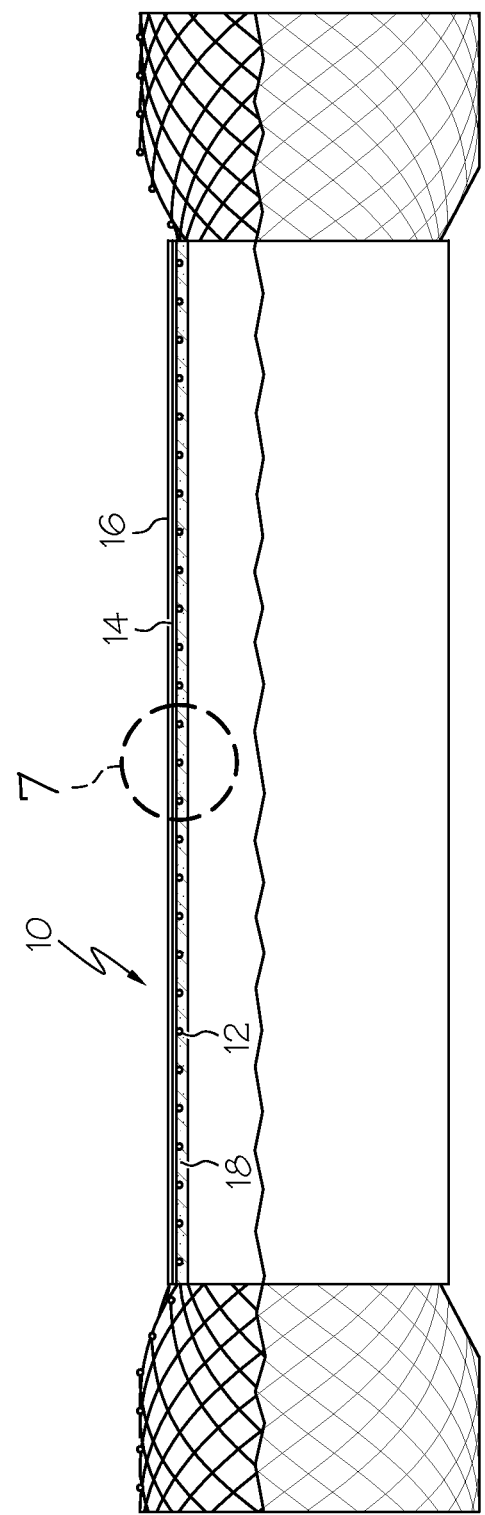
FIG. 6 is a side view of an embodiment of a stent according to the invention.

Turning now to the drawings, FIG. 6 is a side view of one embodiment of a stent on which the coatings according to the invention be employed. In this embodiment, stent 10 is a self-expanding stent formed of a shape memory metal such as Nitinol® having a silicone covering. The stent has a braided wire construction. In this embodiment, stent 10 is shown having a silicone covering 18. Stent 10 is disposed on silicone covering 18 and is partially embedded therein.

Stent 10 may be fully, substantially or partially covered or lined with a polymeric covering 18. The stent 10 may also be embedded in the polymer material. The covering may be in the form of a tubular structure. Nonlimiting examples of useful polymeric materials include polyesters, polypropylenes, polyethylenes, polyurethanes, polynaphthalenes, polytetrafluoroethylenes, expanded polytetrafluoroethylene, silicone, copolymers thereof and mixtures or combinations thereof. Desirably, the polymeric covering 18 is silicone. The polymeric material or silicone 18 may be disposed on the external surfaces of the stent 10, or disposed on the internal surfaces of the stent 10, as depicted in FIGS. 4, 6 and 7, or combinations thereof.

Stents of this type are described in commonly assigned US Patent Publication Nos. 2006/0276887 and 2008/0009934, each of which is incorporated by reference herein in its entirety.

Stent 10 further includes a bioadhesive layer 14 and an outer biodegradable layer 16.

Figure 7:
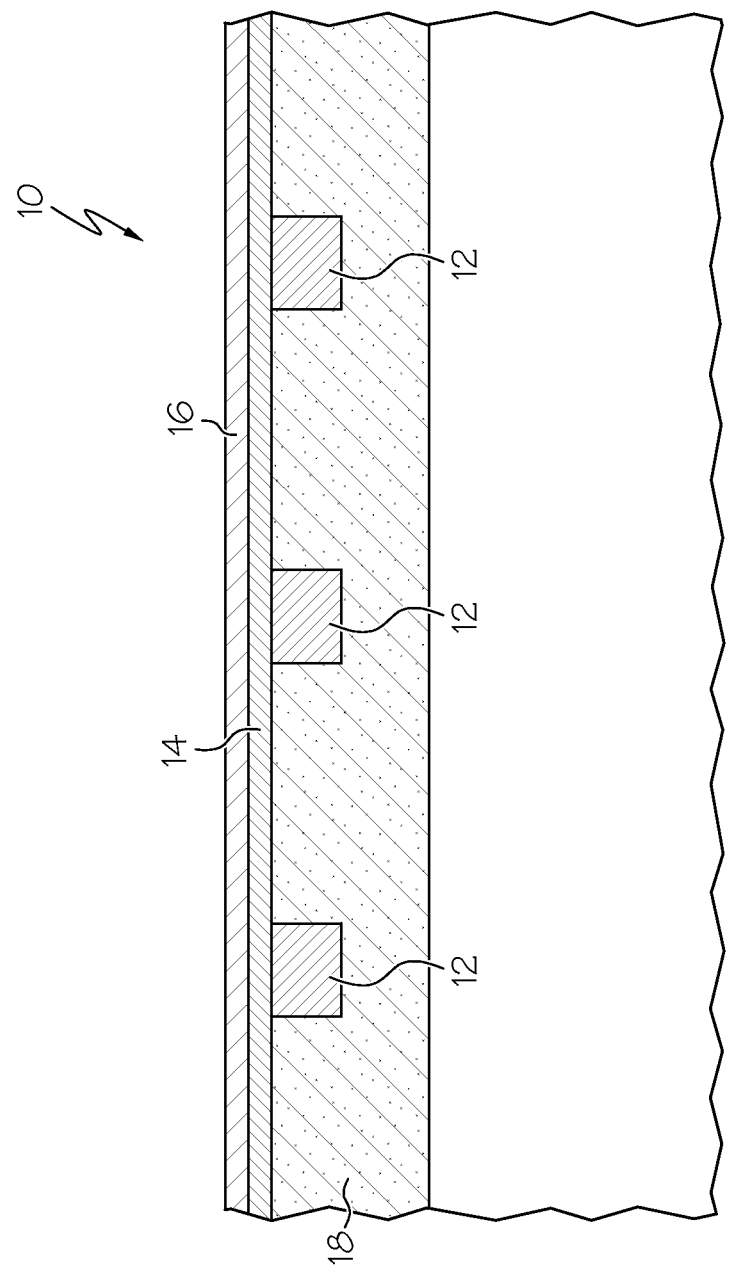
FIG. 7 is a cross-sectional view taken at section 7 in FIG. 6.

FIG. 7 is an enlarged partial cross-sectional view taken at section 6 in FIG. 6 illustrating the tacky polymeric coating on a covered stent 10 according to the invention.

In one embodiment, the stent is a polymeric self-expanding stent formed from polyethylene terephthalate (PET) filaments having a silicone covering. These types of stents are commercially available from Boston Scientific Inc. located in Natick, Mass. under the tradename of POLYFLEX®.

Another example of a covered stent is a self-expanding nitinol stent formed of braided or woven wires and having a silicone covering. These types of stents are commercially available from Boston Scientific Inc. located in Natick, Mass. under the tradename of WALLFLEX®.

Another example of a covered stent is a self-expanding nitinol stent formed of braided or woven wires and having a polyurethane covering. These types of stents are commercially available from Boston Scientific Inc. located in Natick, Mass. under the tradename of ULTRAFLEX®.

Figure 8:
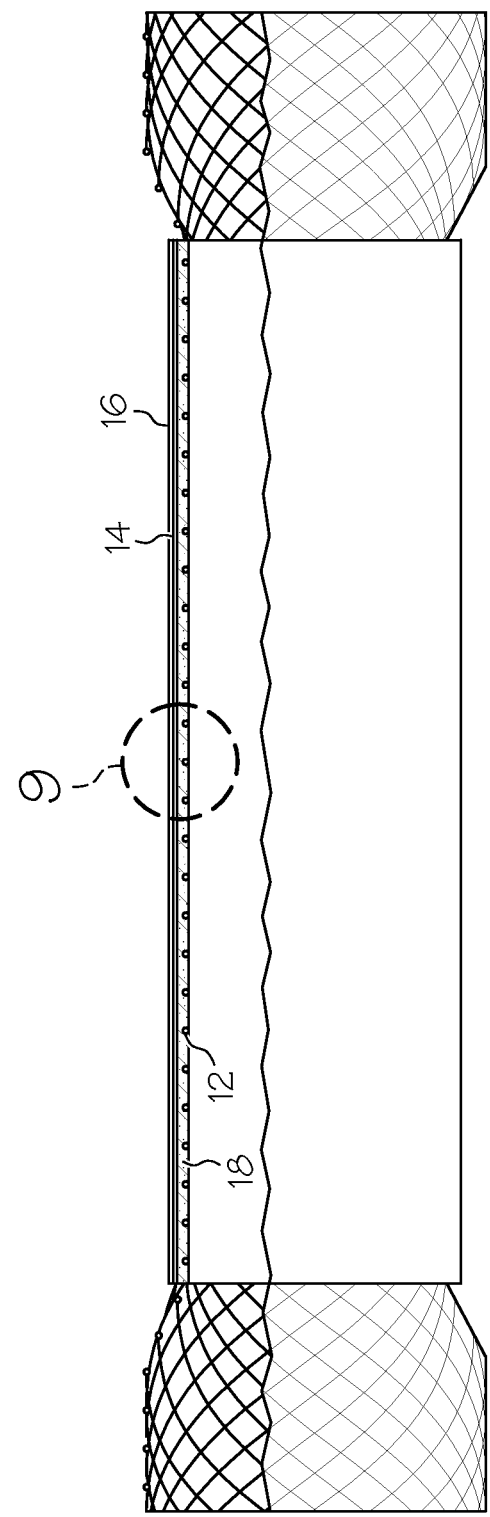
FIG. 8 is a side view of a stent according to the invention.
Figure 9:
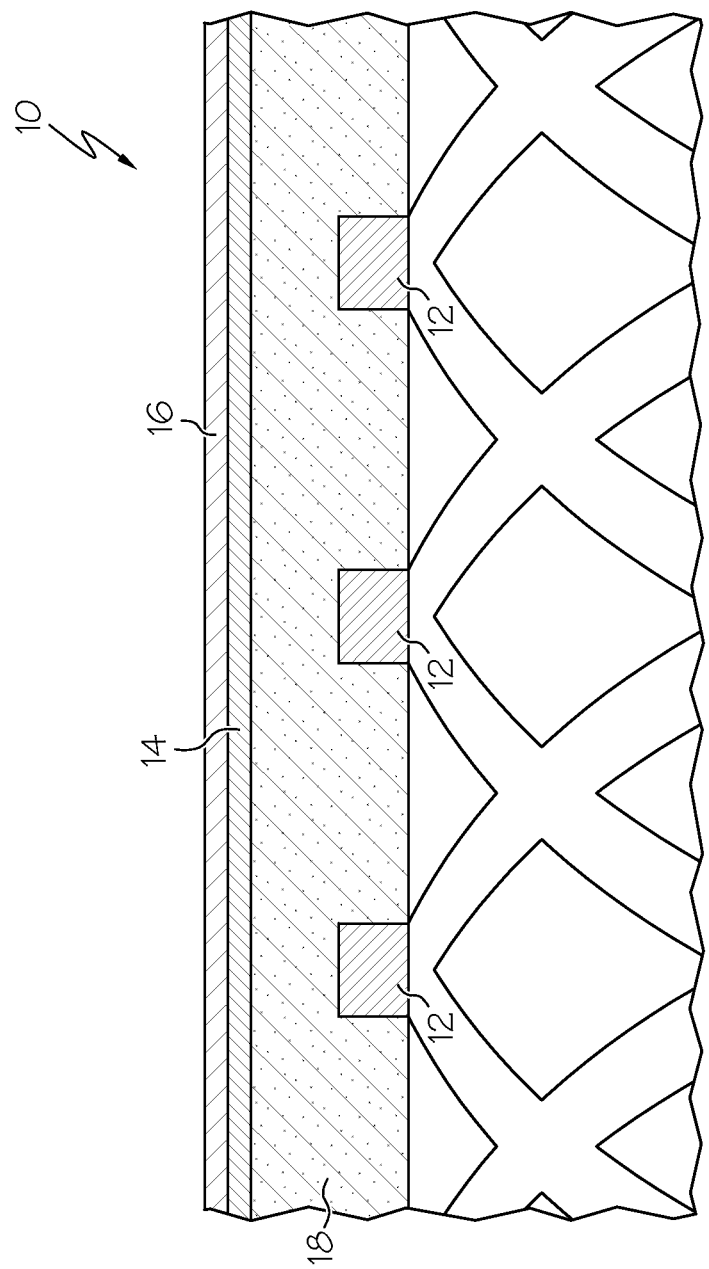
FIG. 9 is a cross-sectional view taken at section 9 in FIG. 8.

FIG. 8 is a side view illustrating covered stents of this type. Stent 10 has a stent wall 12, a silicone covering 18 disposed on the outer surface of stent wall 12, a tacky adhesive coating 14 and a biodegradable coating 16. FIG. 9 is a cross-sectional view of stent 10 taken at section 9 in FIG. 8.

Other suitable covering materials can be employed as well. Examples include, but are not limited to, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

These type of stents are loaded into a catheter delivery system and are maintained therein in an unexpanded state for delivery through a patient's body lumen. Once at the treatment site, and are expanded or deployed at the treatment site.

The bioadhesive layer can encapsulate the entire stent, can be disposed only over a portion of the outer surface of the stent or be disposed on the entirety of the outer surface of the stent. The biodegradable layer may be disposed over the bioadhesive layer.

Any suitable bioadhesive can be employed herein. Bioadhesion refers to the ability of certain materials such as polymers, macromolecules and hydrocolloids to adhere to biological or body tissue.

The bioadhesive material employed herein and can include natural polymeric materials, as well as synthetic materials, and synthetic materials formed from biological monomers such as sugars. Bioadhesives can also be obtained from the secretions of microbes or by marine molluscs and crustaceans. Bioadhesives are designed to adhere to biological tissue.

Examples of bioadhesives include, but are not limited to, mucoadhesives, amino adhesives, adhesive surface proteins (MSCRAMMS), adhesively modified biodegradable polymers such as Fatty Ester Modified PLA/PLGA, polymer materials, hydrogels, minigel particles, and so forth, each discussed in detail below, as well as mixtures thereof.

Amino acids find use in embodiments of the present disclosure. Amino acids can be both utilized to facilitate release from the delivery vehicle as well as to gain adhesion to the lesion site. Zwitterionic amino acids can be employed either as a layer or as a component within the HA/active agent layer. The zwitterionic amino acid can be oriented so that the hydrophobic side of the zwitterionic amino acid selectively facilitates adhesion to the lipophilic lesion. One example of a useful compound is amino acid 3,4-L-dihydroxyphenylalanine (L-DOPA), a tyrosine derivative found in high concentrations in the "glue" proteins of mussels.

Protein adhesions called MSCRAMMs (microbial surface components recognizing adhesive matrix molecules) can also be employed as a bioadhesive in the second coating composition. MSCRAMMS are naturally produced by pathogens to initiate adhesion to the host extra cellular matrix to initiate infection. These adhesive surface proteins can be isolated or synthesized and utilized either as a separate layer or in the HA/active agent composition to facilitate adhesion the lesion site.

In some embodiments, the bioadhesive may include a catechol moiety. Examples include, but are not limited to, L-DOPA, D-DOPA, dopamine or carbidopa.

One example of this type of adhesively modified polymer is able polymers include, but are not limited to, L-DOPA (L-3,4-dihydroxyphenylalanine) modified PLA (polylactic acid) or PLGA poly(lactide-co-glycolide)

In some embodiments, the bioadhesive may include a catechol moiety. Examples include, but are not limited to, L-DOPA, D-DOPA, dopamine or carbidopa. One example of this type of adhesively modified polymer is L-DOPA (L-3,4-dihydroxyphenylalanine) modified PLA (polylactic acid) or PLGA (poly(lactide-co-glycolide) having the following general structure:

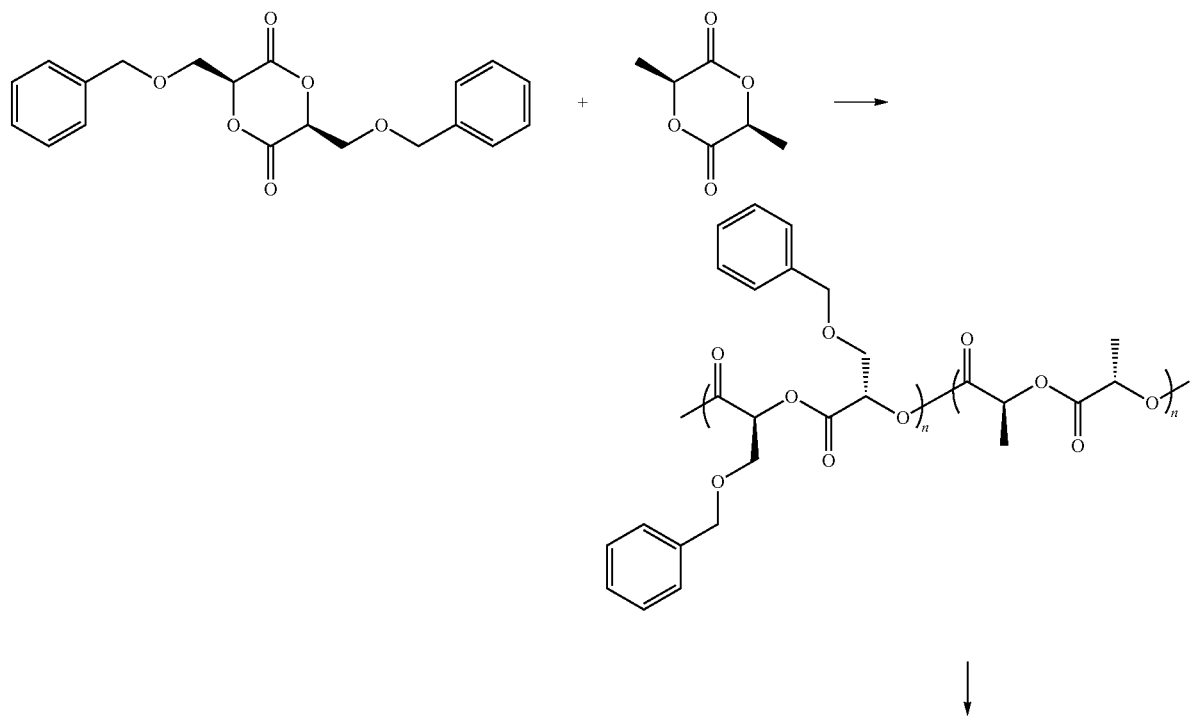

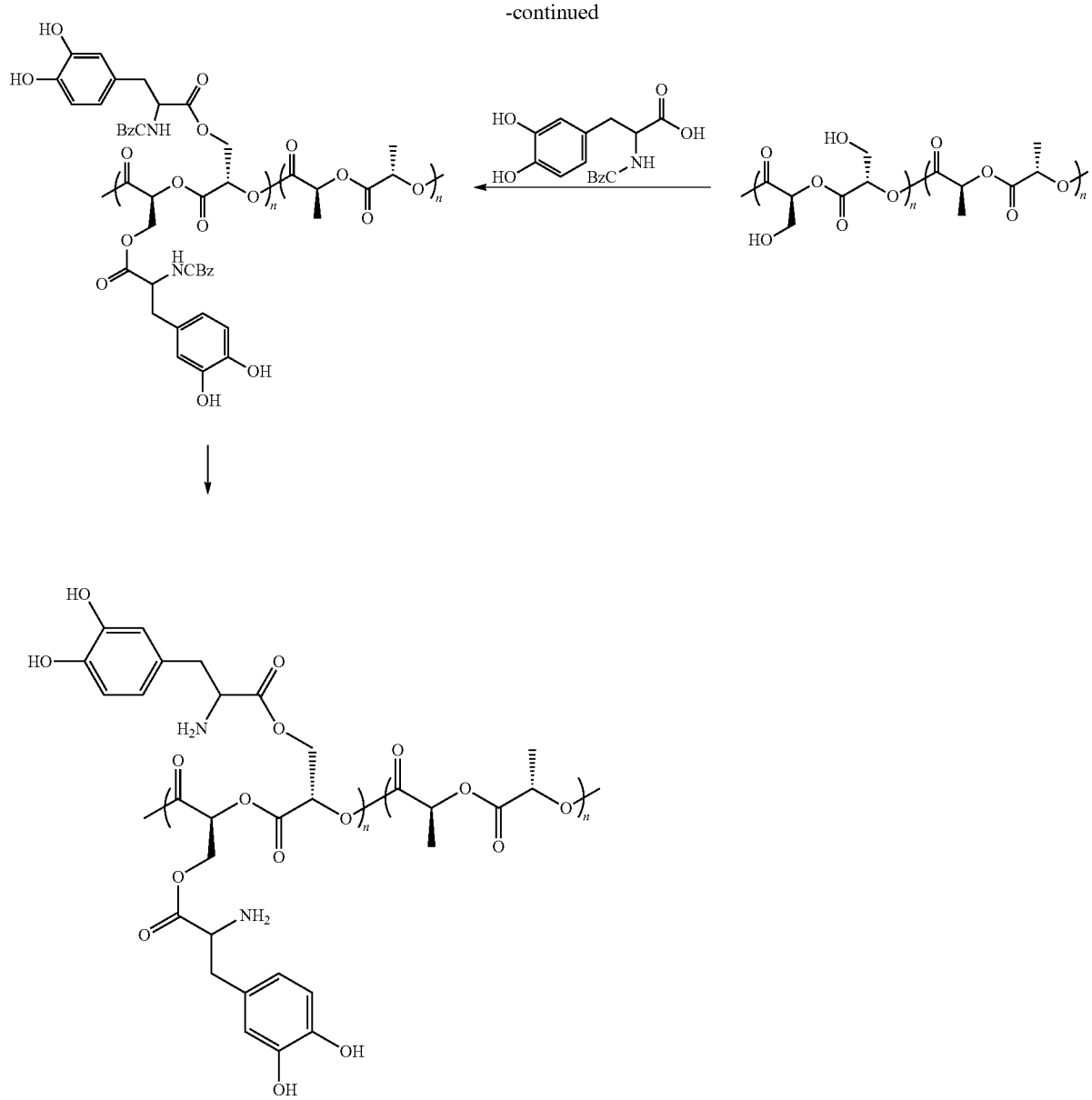
Another example of an adhesively modified biodegradable polymer is a fatty ester modified PLA/PLGA, having the following structure:
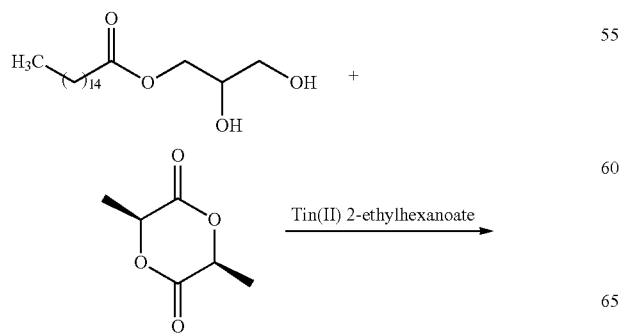
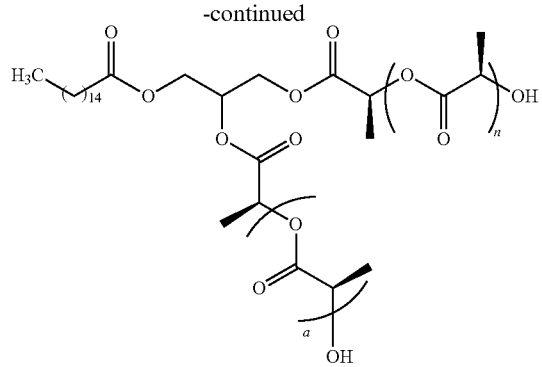
In the above embodiment, other examples of suitable adhesive moieties include, but are not limited to, monopalmitate (shown above), monostearin, glycerol, a,a'-dilaurin or iso-stearyl alcohol.

Another particular class of bioadhesives is the mucoadhesives. The term "mucoadhesive" denotes a compound which exhibits an affinity for a mucosa surface. Mucoadhesive polymers are typically polymers having hydrogen bonding groups. See http://en.wikipedia.org/wiki/Bioadhesive#Mucoadhesion. "Mucoadhesion is the ability of materials to adhere to mucosal membranes in the human body and provide a temporary retention". "Excellent mucoadhesive properties are typical for hydrophilic polymers possessing charged groups and/or non-ionic functional groups capable of forming hydrogen bonds with mucosal surfaces." [*Macromol Biosci.* 2011 Jim 14; 1J(6): 748-64. doi: 10.1002/mabi.201000388.Epub 2010 Dec. 27].

Examples of suitable mucoadhesives include, but are not limited to, polysaccharides including, for example, dextran, dextrane, dextrin, pectin, amylopectin, sorbitol, sucrose, xylitol, anionic hydrated polysaccharides such as gellan, curdlan, XM-6 and xanthan gum (XANTURAL® available from CPKelco, A Huber Company, in Atlanta, Ga.); agar; gums, including, for example, guar gum or locust bean gum; salts of alginic acid such as sodium alginate or magnesium alginate, and hydrated gels thereof; cellulose such as methylcellulose, sodium carboxy methylcellulose, hydroxypropylcellulose (KLUCEL™ available from Ashland in Covington, Ky.); chitosan, proteins such as gelatin; carbohydrates such as starch; and so forth.

Polysaccharides useful herein also include Aloe vera polysaccharides.

Hydrogels find utility herein and include, but are not limited to, polyvinylpyrrolidone (PVP), polyacrylate, chitosan, polyalkylene glycols such as polyethylene glycol (PEG), polyethylene glycol/dextran aldehyde, polyalkylene oxides such as polyethylene oxide and polypropylene oxide, polyvinyl esters such as polyvinyl acetate, polyhydroxyethyl methacrylate, polyvinyl alcohol and polyvinyl ether, polyanions having a high charge density such as crosslinked or non-crosslinked homopolymers and copolymers of (meth) acrylic acid such as Noveon AA-1 Polycarbophil which is an acrylic acid polymer crosslinked with divinyl glycol, copolymers of acrylic acid such as acrylic acid-co-acrylamide copolymers (P(AA-co-AM), and derivatives of polyacrylic acid such as salts and esters thereof, for example, CARBOPOLY® polymers which are homo- and copolymers of acrylic acid crosslinked with a polyalkenyl polyether available from Lubrizol in Wickliffe, Ohio; polymers and copolymers of (meth)acrylic esters; and so forth. Derivatives of many of these polymers may also be employed herein. See for example U.S. Pat. No. 6,391,033, the entire content of which is incorporated by reference herein.

Hydrogels are disclosed in commonly assigned U.S. Pat. No. 5,693,034 to Buscemi et al.

For a discussion of polyacylic acid mucoadhesion see *Mechanisms of Mucoadhesion of Poly(acrylic Acid) Hydrogels*, by Haesun Park and Joseph R. Robinson, Pharmaceutical research, 1987, Vol 4, No 6, 457-464.

Another bioadhesive is poly(NIPAM) (poly(N-isopropylacrylamide) minigel particles. This polymer has the property of being in a liquid state at room temperature and an adhesive at body temperature. See *"Preparation and Swelling Properties of Poly(NIPAM) "Minigel" Particles Prepared by Inverse Suspension Polymerization"*, Dowding, John et al., *Journal of Colloid and Interface Science* 221, 268-272 (2000), available online at http:/www.idealibrary.com, the entire content of which is incorporated by reference herein.

For better retention to a medical device surface, several techniques may be employed. Suitably, the minigel particles are crosslinked or mixed with a higher molecular weight polymer to allow enough time for retention of the minigel to the medical device during delivery, or uncrosslinked minigel particles can be employed in a crosslinked polymer network.

For example, an uncrosslinked minigel such as poly(N-isopropylacrylamide) may be employed with the reaction product of a vinyl polymer. See commonly assigned U.S. Pat. No. 5,693,034, the entire content of which is incorporated by reference herein.

Poly(N-isopropylacrylamide) may also be blended with a higher molecular weight polymer such as a higher molecular weight hydrogel polymer. Examples of hydrogels that may be blended with poly(n-isopropylacrylamide) include, but are not limited to, polyvinylpyrrolidone, polyacrylamides, polyethylene oxide, polyacrylic acid, poly(sodium-4-styrenesulfonate), poly(3-hydroxybutyric acid), and 2-hydroxyethyl methacrylate.

These bioadhesives are disclosed in commonly assigned copending US Patent Publication No. 2012-0095396, filed Aug. 16, 2011 and claiming the benefit of U.S. Provisional Patent Application No. 61/394,104 filed Oct. 18, 2010, the entire content of which is incorporated by reference herein.

Another mucoadhesive, xyloglucan, is disclosed in US Patent Publication No. 20120088726 which is incorporated by reference herein in its entirety. Glycerol, which can be employed in combination with any of the above mucoadhesives, has been found to increase the mucoadhesiveness of xyloglucan.

Other bioadhesives are also disclosed in US Patent Publication No. 2010/00316712, and in Tao et al., "Bioadhesive poly(methyl methacrylate) microdevices for controlled drug delivery", Journal of Controlled Release, 88, (2003), 215-228; Sekiyama et al., "Novel Sutureless Transplantation of Bioadhesive-Coated, Freeze-Dried Amniotic Membrane for Ocular Surface Reconstruction", Investigative Ophthalmology & Visual Science, April 2007, Vol. 48, No. 4, 1528-1534; and Lim et al., "The adhesive properties of coacervated recombinant hybrid mussel adhesive proteins", Biomaterials, 31, (2010), 3715-3722 each of which is incorporated by reference herein in its entirety.

These lists are intended for illustrative purposes only, and not as a limitation on the scope of the present invention.

Any biodegradable material can be employed herein that does not form an adhesive layer. These biodegradable materials break down and lose their integrity in vivo. Examples of suitable biodegradable polymers include, but are not limited to, poly(amides) such as poly(amino acids) and poly(peptides), poly(esters) such as polylactide including poly(DL-lactide) and polyglycolide, and copolymers thereof such as polylactide-co-glycolide including poly(DL-lactide-co-glycolide), poly(L-lactide-co-glycolide), poly(caprolactone) and polylactide-co-caprolactone including poly(DL-lactide-co-caprolactone and poly(L-lactide-co-caprolactone), poly(anhydrides), poly(orthoesters), poly (carbonates) including tyrosine derived polycarbonates, polyhydroxyvalerate, polyhydroxybutyrate, polyhydroxybutyrate-co-valerate, and chemical derivatives thereof (substitutions, additions of chemical groups, for example, alkyl, alkylene, hydroxylations, oxidations, and other modifications routinely made by those skilled in the art), copolymers and mixtures thereof.

Biodegradable metallic elements can also be employed herein. Examples include, but are not limited to, iron (Fe) and magnesium (Mg) and alloys thereof. Examples of suitable biodegradable metal alloys include, but are not limited to, Fe30Mn (Mn=manganese) and Fe30Mn6Si (Si=silicon).

These lists are intended for illustrative purposes only, and not as a limitation on the scope of the present invention.

Some of the bioadhesives may form a permanent coating on the stent while others will form a temporary coating on the stent. In cases wherein it is desirable to remove the stent after treatment, it may be desirable to select a temporary bioadhesive.

For example, hydrogels and proteins, carbohydrates, glycoproteins and mucopolysaccharides which can be used for form hydrogels, may be used where temporary adhesion is desirable.

Permanent bioadhesives can be crosslinked materials that are generated via a "mix to activate" process.

L-DOPA, discussed above, can be used to form a covalently crosslinked permanent bioadhesive on the surface of the medical device.

While it is preferable to employ a biodegradable coating layer over the bioadhesive layer, for some bioadhesives it may be possible to employ them without the biodegradable coating layer.

Therapeutic agents may be incorporated in the bioadhesive coating layer, the biodegradable coating layer, or both.

Various therapeutic agents may be employed herein depending on the condition which is being treated. As used herein, the terms, "therapeutic agent", "drug", "pharmaceutically active agent", "pharmaceutically active material", "beneficial agent", "bioactive agent", and other related terms may be used interchangeably herein and include genetic therapeutic agents, non-genetic therapeutic agents and cells. A drug may be used singly or in combination with other drugs. Drugs include genetic materials, non-genetic materials, and cells.

A therapeutic agent may be a drug or other pharmaceutical product such as non-genetic agents, genetic agents, cellular material, etc. Some examples of suitable non-genetic therapeutic agents include but are not limited to: antithrombogenic agents such as heparin, heparin derivatives, vascular cell growth promoters, growth factor inhibitors, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof.

Other active agents include, but are not limited to, antineoplastic, antiproliferative, antimitotic, antiinflammatory, antiplatelet, anticoagulant, antifibrin, antiproliferative, antibiotic, antioxidant, and antiallergic substances as well as combinations thereof.

Examples of antineoplastic/antiproliferative/antimitotic agents include, but are not limited to, paclitaxel (e.g., TAXOL® by Bristol-Myers Squibb Co., Stamford, Conn.), the olimus family of drugs including sirolimus (rapamycin), biolimus (derivative of sirolimus), everolimus (derivative of sirolimus), zotarolimus (derivative of sirolimus) and tacrolimus, methotrexate, azathiprine, vincristine, vinblastine, 5-fluorouracil, doxorubicin hydrochloride, mitomycin, cisplatin, vinblastine, vincristine, epothilones, endostatin, angiostatin and thymidine kinase inhibitors. While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions. See commonly assigned U.S. Patent Application Nos. 2010/0087783, 2010/0069838, 2008/0071358 and 2008/0071350, each of which is incorporated by reference herein. See also commonly assigned U.S. Patent Application Nos. 2004/0215169 and 2009/0098176, and U.S. Pat. No. 6,805,898, each of which is incorporated by reference herein.

Derivatives of many of the above mentioned compounds also exist which are employed as therapeutic agents and of course mixtures of therapeutic agents may also be employed.

For application, the therapeutic agent can be dissolved in a solvent or a cosolvent blend along with the bioadhesive or biodegradable polymer material.

Suitable solvents include, but are not limited to, dimethyl formamide (DMF), butyl acetate, ethyl acetate, tetrahydrofuran (THF), dichloromethane (DCM), acetone, acetonitrile, dimethyl sulfoxide (DMSO), butyl acetate, etc.

The stents according to the invention are manufactured using any conventional method which may first involve extrusion of a tubular member or folding of a sheet of a suitable material and the cutting a stent pattern therein such as with laser cutting, etching or the like. Braided stents also find utility herein.

The stent may be coated with the bioadhesive material by first dissolving the material in a suitable solvent or cosolvent blend and then coating the stent by spraying, dipping, painting or the like.

Suitable polar solvents include, but are not limited to, alcohols including methanol, ethanol and isopropanol, and water.

Other suitable solvents include tetrahydrofuran, chloroform, toluene, acetone, isooctane, 1,1,1-trichloroethane, or a mixture thereof. Acetone can be employed with either polar or non-polar systems and is readily blended with both types of solvents.

The stent is then coated with the outer biodegradable layer by dissolving the material in a suitable solvent and then coating by spraying, brushing, painting or the like.

Examples of specific coating techniques that can be employed herein include, but are not limited to, Drop-on-Demand coating techniques, MicroPen coating techniques and $M^3D$ direct-write coating technologies.

The bioadhesive can be applied to the stent so as to encapsulate the entire stent, to coat only the outside surface/diameter of the stent or coat specific regions of the stent, for example, the stent flares.

In one embodiment, the stent is provided with cavities/holes/well/pockets wherein the bioadhesive is disposed in the cavities and the biodegradable coating is applied over the top thereof to seal the bioadhesive in the cavities.

Alternatively, the stent may be coated with a silicone coating prior to application of the bioadhesive.

The stent is then loaded into the stent delivery system using conventional stent loading techniques.

The adhesive layer provides adhesion between the stent and the lumen and/or lesion. The outer biodegradable polymer layer prevents self-adhesion of the bioadhesively coated stent during handling, storage and delivery in situ.

The outer biodegradable polymer layer also allows the stent to be loaded into a delivery system in any conventional manner.

Once the stent is deployed in the patient's body, the biodegradable polymer layer erodes, exposing the bioadhesive layer which provides adhesion of the stent at the desired treatment site thus preventing undesirable stent migration.

The coatings can be employed on any stent including, but not limited to, endoscopic, pulmonary and vascular stents.

Examples of endoscopic stents include, but are not limited to, esophageal, pancreatic, gastrointestinal and biliary stents. A specific example of a stent on which the coatings of the invention can be employed is on the POLYFLEX® esophageal stent available from Boston Scientific. POLYFLEX® stents are described in commonly assigned US Patent Publication No. 2009/00082840, the entire content of which is incorporated herein by reference. Methods of loading the stents into a delivery device are also disclosed therein.

The invention may also be employed on urethral, ureteral and tracheal stents.

The above lists are intended for illustrative purposes only, and not as a limitation on the scope of the present invention.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A stent comprising:
a stent body having a proximal end portion, a distal end portion, and a length extending therebetween, the stent body having an inner surface and an outer surface;
a first coating layer disposed on said stent body, said first coating layer comprising at least one bioadhesive disposed on at least a portion of the outer surface of the stent body, wherein said at least one bioadhesive is a mucoadhesive;
a second coating layer disposed over the first coating layer, the second coating layer comprising at least one biodegradable material that loses integrity in vivo to expose the first coating layer, the second coating layer forming a substantially continuous layer over an entirety of the first coating layer; and
a silicone coating located radially inward relative to said first coating layer, wherein the first coating layer directly contacts both the stent body and the silicone coating.

2. The stent of claim 1 wherein said mucoadhesive comprises at least one member selected from the group consisting of homo- and copolymers of acrylic acid and crosslinked acrylic acid, polysaccharides, cellulose and mixtures thereof.

3. The stent of claim 1 wherein said mucoadhesive comprises a hydrogel.

4. The stent of claim 1 wherein said at least one biodegradable material that loses integrity in vivo is a polymer comprising at least one member selected from the group consisting of polylactide and polylactide-co-glycolide.

5. The stent of claim 1 wherein said at least one biodegradable material that loses integrity in vivo comprises a biodegradable metallic element.

6. The stent of claim 5 wherein said at least one biodegradable metallic element comprises at least one of iron and magnesium and alloys thereof.

7. The stent of claim 1 wherein said stent body is encapsulated by the first coating layer.

8. The stent of claim 1 wherein the first coating layer is disposed on an entirety of the outer surface of the stent body.

9. The stent of claim 1 wherein said at least one bioadhesive is crosslinked.

10. The stent of claim 1, wherein the proximal and distal end portions of the stent body include flared end portions, wherein the first coating layer is disposed only on the flared end portions.

11. A stent, the stent comprising:
a stent body having a proximal end portion, a distal end portion, and a length extending therebetween, the stent body having an inner surface and an outer surface;
a first coating composition disposed on said stent body, said first coating composition comprising at least one temporary bioadhesive, the temporary bioadhesive is a natural polymeric material or a synthetic polymer material formed from a sugar;
a second coating composition disposed over and contacting the first coating composition, the second coating composition comprising at least one biodegradable material that loses integrity in vivo to expose the first coating composition, the second coating composition forming a substantially continuous layer over an entirety of the first coating composition; and
a silicone layer directly contacting both the stent body and the first coating composition, wherein the first coating composition contacts both the stent body and the silicone layer.

12. The stent of claim 11, wherein said at least one biodegradable material that loses integrity in vivo is a polymer comprising at least one member selected from the group consisting of polylactide and polylactide-co-glycolide.

13. The stent of claim 11, wherein said at least one biodegradable material that loses integrity in vivo comprises a biodegradable metallic element.

14. The stent of claim 11, wherein the proximal and distal end portions of the stent body include flared end portions, wherein the first coating composition is disposed only on the flared end portions.

15. A stent comprising:
a stent body having a flared proximal end portion, a flared distal end portion, and a length extending therebetween, the stent body having an inner surface and an outer surface and a plurality of openings extending through the stent body from the inner surface to the outer surface;
a single bioadhesive layer surrounding only the flared proximal and distal end portions of the stent body and having an inner surface and an outer surface;
a biodegradable layer surrounding the single bioadhesive layer and contacting the outer surface of the single bioadhesive layer; and
a silicone covering disposed on the inner surface of the stent body, the silicone covering being located radially inward relative to the single bioadhesive layer and contacting the inner surface of the single bioadhesive layer, wherein the single bioadhesive layer directly contacts both the stent body and the silicone covering.

16. The stent of claim 15, wherein the silicone covering is a tubular structure and the inner surface of the single bioadhesive layer surrounding the stent body directly contacts a portion of an outer surface of the silicone covering available through the plurality of openings.

17. The stent of claim 15, wherein the silicone covering contacts the stent body and is located in the openings of the stent body.

18. The stent of claim 15, wherein the single bioadhesive layer includes a temporary bioadhesive.

19. The stent of claim 18, wherein the temporary bioadhesive includes a mucoadhesive.

20. The stent of claim 15, wherein said biodegradable layer includes a biodegradable metallic element.

* * * * *